United States Patent [19]

Warden

[11] 4,455,668

[45] Jun. 19, 1984

[54] X-RAY EXAMINATION APPARATUS

[75] Inventor: Hans Warden, Upplands-Vaesby, Sweden

[73] Assignee: Siemens Aktiengesellschaft, Berlin and Munich, Fed. Rep. of Germany

[21] Appl. No.: 393,110

[22] Filed: Jun. 28, 1982

[30] Foreign Application Priority Data

Jul. 24, 1981 [DE] Fed. Rep. of Germany ....... 3129307

[51] Int. Cl.³ .......................... A61B 6/02; G01T 1/29
[52] U.S. Cl. ...................................... 378/021; 378/24
[58] Field of Search ...................... 378/21, 22, 25, 26, 378/23, 24, 27

[56] References Cited

U.S. PATENT DOCUMENTS 2,789,231  4/1957  Dumer ................................. 378/24

OTHER PUBLICATIONS

Siemens–Elema AB Brochure, "Mimer III", six pp.

Primary Examiner—Alfred E. Smith
Assistant Examiner—T. N. Grigsby
Attorney, Agent, or Firm—Hill, Van Santen, Steadman & Simpson

[57] ABSTRACT

An exemplary embodiment comprises a support pivotal about a shaft which, on one side of the shaft, is provided with an x-ray tube, and on the other side, is provided with an arrangement for the adjustment of an image recording carrier along the support. In order to produce an x-ray examination apparatus in which, in the case of a tomography examination, the central x-ray always strikes the film center, independently of the subject-to-film-distance, it is provided in accordance with the disclosure that the arrangement is comprised to two toothed racks running parallel to the longitudinal direction of the support, into which, in the shaft region, two rigidly interconnected gear wheels, or gear wheel segments, engage, which are selectively arrestable relative to different parts of the apparatus, and into which, in the region of the image recording carrier, two intermeshed gear wheels engage with which the image recording carrier is at least indirectly connected, as well as comprising a motor for the displacement of the gear wheels along the toothed racks.

7 Claims, 3 Drawing Figures

X-RAY EXAMINATION APPARATUS

BACKGROUND OF THE INVENTION

The invention relates to an x-ray examination apparatus, comprising a support which is pivotal about a shaft which support is provided, on one side of the shaft, with an x-ray tube, and on the other side, with an arrangement for the adjustment of an image recording carrier along the support.

An x-ray apparatus of this type is known from the Elema-Schoenander-Brochure "Mimer III". With this apparatus radiographs can be effected perpendicularly to the roentgencentral ray in every angular position of the stand with the image recording carrier, for example a cassette support-mounting with a cassette. The height adjustment of the cassette support-mounting proceeds on a column which is mounted in a shaft on the support. With the apparatus, furthermore, tomography-records can be made in that the cassette support-mounting, always oriented parallel to a patient lying on an examination table, during pivoting the stand, describes an arcuate movement. This takes place in that the column, even in an inclined position of the support, is always positioned perpendicularly to the patient. When the cassette support-mounting is applied in the region of the shaft of the column, the central x-ray, traversing the pivot axis of the support, impinges on the center of the cassette support-mounting. For a satisfactory tomography examination, the region of the patient to be examined must be disposed at the level of the pivot axis. However, the requirement exists of reducing the subject-to-film distance in order that more sharply defined radiographs are obtained. This is achieved in that the cassette support-mounting is upwardly displaced on the column. The disadvantage with such a displacement of the cassette support-mounting lies in that the central x-ray, given an inclined position of the support, no longer strikes the center of the film cassette support mounting, or of the film cassette, respectively. This leads to the result that the x-ray beam, laterally restricted by an x-ray diaphragm, does not entirely cover the film. Moreover, this leads to a certain loss of definition in the radiograph.

SUMMARY OF THE INVENTION

The object underlying the invention resides in producing an x-ray examination apparatus of the type initially cited wherein, in the case of a tomography examination, the central x-ray always strikes the film center, independently of the subject-to-film-distance.

In accordance with the invention, this object is achieved in that the arrangement is comprised of two toothed racks running parallel to the longitudinal direction of the support, with which toothed racks, in the shaft region, two rigidly interconnected gear wheels, or gear wheel segments, engage, which are capable of being selectively arrested or fixed relative to different parts of the apparatus, and with which toothed racks, in the region of the image recording carrier, two interengaged gear wheels engage, with which interengaged gear wheels the image recording carrier is at least indirectly connected, as well as comprising means for the displacement of the gear wheels along the toothed racks. Through the arrangement, with each change of the film-to-subject-distance, the image recording carrier is so driven along the support that the film is always moved along the central x-ray.

In an advantageous further development of the invention, it is proposed that the two rigidly interconnected gear wheels, or gear wheel segments, respectively, are capable of being arrested (or locked) in a spatially fixed fashion. It is thereby achieved that a tomography examination can be conducted from a randomly angled initial position of the support. It has the advantage that the patient, in the case of certain examinations, need not be brought into uncomfortable positions, but can be comfortably supported in the supine position or in the prone position.

In a further development of the invention it is proposed that the two rigidly interconnected gear wheels, or gear wheel segments, respectively, be stationarily arrestable on the support. It is thereby achieved that the x-ray examination apparatus can be converted from a tomography examination apparatus into a conventional x-ray examination apparatus in which the image recording carrier is disposed in each position of the support perpendicularly to the central x-ray.

Further advantages and details of the invention are apparent from the subclaims.

The invention shall be explained in greater detail in the following on the basis of an exemplary embodiment illustrated on the accompanying drawing sheets; and other objects, features and advantages will be apparent from this detailed disclosure and from the appended claims.

DETAILED DESCRIPTION

Figure 1:
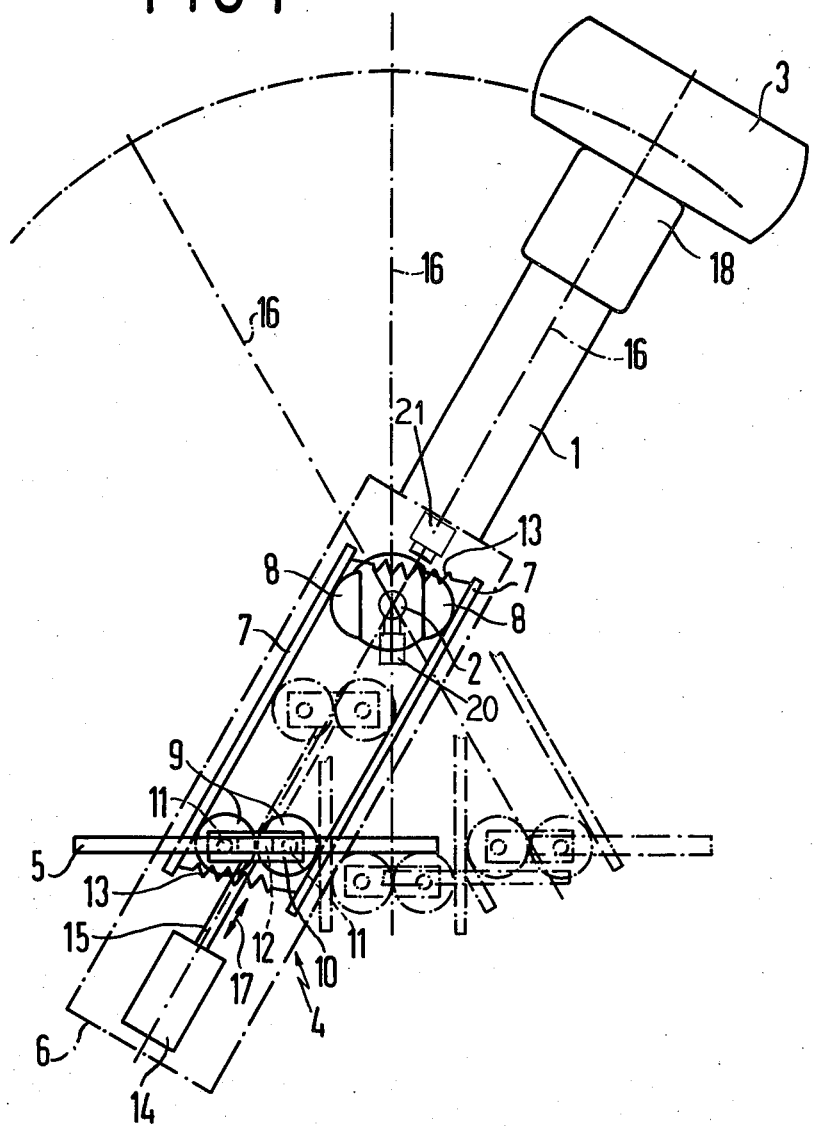
FIG. 1 illustrates a schematic representation of an x-ray examination apparatus, comprising an arrangement for the adjustment of an image recording carrier in accordance with the invention, during tomographic operation.

In the Figures, an x-ray examination apparatus, designed for pivotal support, is illustrated with which conventional radiographs as well as tomography records can be effected. In FIG. 1, the x-ray examination apparatus has been adjusted with means to be described later such that tomography records can be made. The x-ray examination apparatus exhibits a support 1 which is pivoted about a shaft 2. The support 1 is provided, on the one side of the shaft 2, with an x-ray tube 3, and on the other side, with an arrangement 4 for the adjustment of an image recording carrier 5, for example a film cassette, along the support 1.

The arrangement for the adjustment of the film cassette 5 along the support 1 is comprised of two toothed racks 7, arranged in a housing 6, and extending parallel to the longitudinal direction of the support 1. In the region of the shaft 2 of the support 1 two rigidly interconnected gear wheel segments 8 engaged with the respective racks 7. The gear wheel segments 8 are selectively arrestable relative to different parts of the apparatus. In the example illustrated in FIG. 1, the gear wheel segments 8 are arrested to maintain the illustrated horizontal disposition independently of the pivotal movement of the support 1, i.e. the gear wheel segments 8 are fixed stationarily, with known and therefore not illustrated means. Between the toothed racks 7 two gear wheels 9 are arranged which are in engagement with one another and with a respective one of the toothed racks 7. The gear wheels 9 are interconnected by a plate 10 which is secured to the respective axles 11 of the gear wheels 9. The cassette support-mounting 5 is mounted via a support-mounting 12 (FIG. 3) on the plate 10. In addition, the toothed racks 7 are flexibly interconnected by means of tension springs 13.

For the displacement of the cassette support-mounting 5 along the support 1 an electric motor 14 is provided which controls a bar 15, whose free end is mounted on the plate 10 and which is movable in the direction of the arrow 17 to shift the plate 10.

Figure 3:
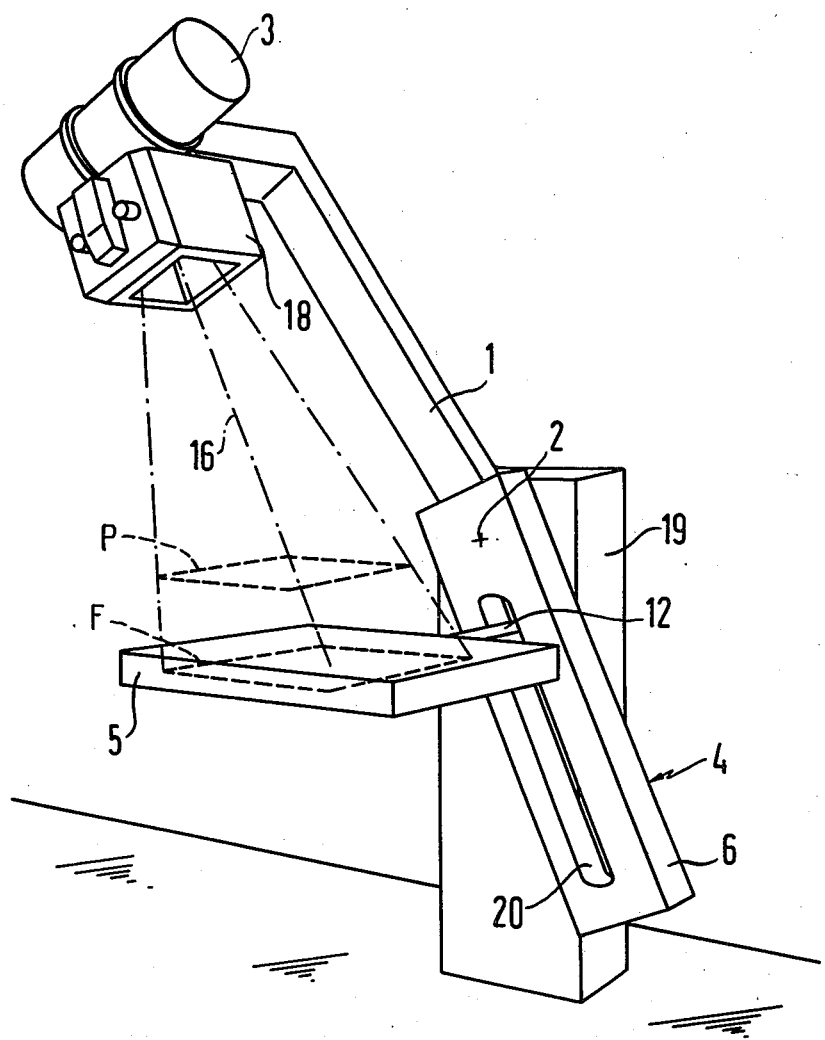
FIG. 3 illustrates a perspective view of an x-ray examination apparatus according to FIGS. 1 and 2.

In a tomography examination, the region to be recorded of a non-illustrated patient, or the subject plane P, FIG. 3, lies at the level of the shaft 2 of the support 1. The subject is recorded while the support 1 with the x-ray tube 3 is pivoted about the shaft 2 to predetermined angular positions. In FIG. 1, various angular positions of the central x-ray 16 and a part of the arrangement 4 with the cassette support-mounting 5 during a pivoting cycle of the support 1 are indicated in dash-dot lines. The arrangement 4 functions like a parallelogram system in which the toothed racks 7, during pivoting of the support 1 about the shaft 2, roll on the respectively associated toothed segment 8. In the same manner, the toothed racks 7 roll on the gear wheels 9, engaged with the latter, in such a fashion that the gear wheels 9, together with the cassette support-mounting 5, describe a parallel movement in space with the same distance to the shaft 2.

When the subject-to-film-distance is to be reduced, the gear wheels 9 are guided by means of the rod 15 along the toothed racks 7 until the desired distance has been attained. The cassette support-mounting 5 is thus displaced along the support 1 in such a fashion that the central ray 16 of the x-ray tube 3 is always disposed in the center of a film-receiving region F, FIG. 3, and the cassette support-mounting 5 is always disposed parallel in comparison to its original position. In this manner, the x-ray beam, generated by the x-ray tube 3, and bounded by a diaphragm 18, will cover the film in every position. Through the toothed segments 8, rotatable and arrestable (capable of being fixed) in any desired position, a tomography examination can proceed from any random angular position. This has the advantage that the patient during such an examination can always be supported in a position which is comfortable for him.

Figure 2:
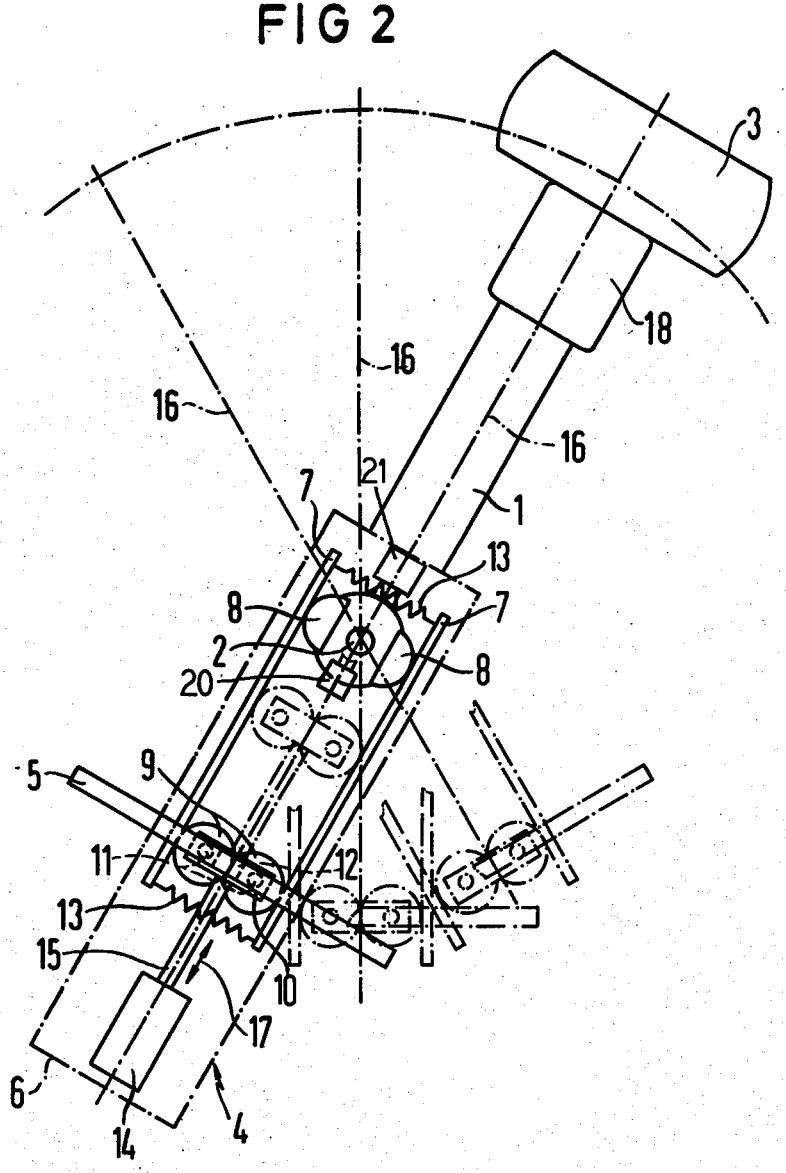
FIG. 2 illustrates a further development possibility of the image recording carrier by means of the arrangement according to FIG. 1, and which conditions the apparatus for a conventional x-ray operation.

In FIG. 2 it is shown that radiographs can also be effected in every angular position of the support 1 with the cassette support-mounting 5 always perpendicular to the central x-ray 16. This proceeds in that the gear wheel segments 8 have been stationarily arrested on the support 1. Given a pivot movement of the support 1 about the shaft 2, the parts 7 through 13 of the arrangement 4 retain their positions relative to one another in every angular position of the support. This is apparent from the parts of the arrangement and cassette support-mounting 5 illustrated in dot-dash lines. The cassette support-mounting 5 can also be displaced along the support 1 in this position in the described fashion by means of the motor 14 and the bar 15.

The x-ray examination apparatus can be suspended by a ceiling support or also can include a support resting on the floor via a column 19 such as is illustrated in FIG. 3. In this Figure, in which the cassette support-mounting is adjusted for tomography recording, it is illustrated that the support-mounting 12 of the cassette support-mounting 5 runs in a track 20 defined by an elongated slot in the housing 6.

It will be apparent that many modifications and variations may be made without departing from the scope of the teachings and concepts of the present invention.

SUPPLEMENTARY DISCUSSION

For the sake of diagrammatic illustration, FIG. 1 shows a locking device 20 fixed to the gear segments 8 and engaged with shaft 2 which in this case acts as a fixed (non-rotary) element on which the support 1 and the housing 6 pivot as a unit.

Also for the sake of diagrammatic illustration, in FIG. 2, a locking device 21 secured to housing 6 is shown as engaged with gear segments 8 to cause the gear segments to pivot on shaft 2 jointly with support 1 and housing 6.

I claim as my invention:

1. X-ray examination apparatus, comprising a support pivotal about a pivot axis, and having on one side of the pivot axis an x-ray source, and on the other side, having an image recording carrier, and an arrangement for the adjustment of the image recording carrier along the support, characterized in that the arrangement (4) comprises two toothed racks (7) running parallel to the longitudinal direction of the support (1), two rigidly interconnected gear wheels, or gear wheel segments, (8) at the region of the pivot axis (2) and engaged with the racks (7) and adapted to be locked selectively relative to different parts of the apparatus, and in the region of the image recording carrier (5) two intermeshed gear wheels (9) for coupling with the image recording carrier (5) at least indirectly, and means (14,15) for the displacement of the gear wheels along the toothed racks to adjust the position of the image recording carrier (5).

2. X-ray examination apparatus according to claim 1, characterized in that the two rigidly interconnected gear wheels, or gear wheel segments (8), respectively, are arrestable in a spatially fixed fashion.

3. X-ray examination apparatus according to claim 1, characterized in that the two rigidly interconnected gear wheels, or gear wheel segments (8), respectively, are arrestable stationarily on the support (1).

4. X-ray examination apparatus according to claim 1, characterized in that the toothed racks (7) are flexibly interconnected.

5. X-ray examination apparatus according to claim 1, characterized in that the gear wheels (9) are interconnected via at least one plate (10) which is secured to the respective axles (11) of the gear wheels (9).

6. X-ray examination apparatus according to claim 5, characterized in a support-mounting (12) for the image recording carrier (5) connected with the plate (10) for adjustment therewith.

7. X-ray examination apparatus according to claim 1, characterized in that there are provided, as means for the displacement, a mechanical force source (14) and a bar (15), for transmitting the force, which engages at least with one gear wheel (9).

* * * * *